United States Patent [19]

Weltman et al.

[11] 4,121,157
[45] Oct. 17, 1978

[54] CASTABLE MAGNETIC PARTICLE FLAW DETECTION COMPOSITION AND METHOD USING CONSTITUENTS THAT ARE NON-VOLATILE AND RESISTANT TO OXIDATION BELOW 100° F AND HAVING A VISCOSITY LESS THAN 12,000 CENTIPOISES

[75] Inventors: Henry J. Weltman; Mark T. Carroll; John E. Halkias; William T. Kaarlela; Jack D. Reynolds, all of Fort Worth, Tex.

[73] Assignee: General Dynamics Corporation, Fort Worth, Tex.

[21] Appl. No.: 812,873

[22] Filed: Jul. 5, 1977

[51] Int. Cl.$^2$ ............................................. G01R 33/12
[52] U.S. Cl. ................................. 324/216; 252/62.52
[58] Field of Search ....................... 324/214, 215, 216; 252/62.52, 62.53, 62.54

[56] References Cited

U.S. PATENT DOCUMENTS

| 3,862,047 | 1/1975 | Weltman et al. | 324/216 |
| 3,978,398 | 8/1976 | Molina | 324/216 |

Primary Examiner—Robert J. Corcoran

Attorney, Agent, or Firm—James C. Fails; Charles E. Schurman

[57] ABSTRACT

A method for forming and preserving a permanent record of inspections of workpieces or the like having drilled holes or other metallic surface conformations characterized by applying a castable, plural component, magnetically active material comprised of room temperature vulcanizing, or polymerizing, rubber containing magnetizable particles and specific sensitizing agents; magnetizing the area to be inspected, so as to cause migration of the particles in the rubber before the viscosity becomes too high for the magnetized particles to migrate to the situs of an imperfection, or flaw; forming a magnetic rubber inspection replica or record of the alignment of the magnetizable particles adjacent the interface between the casting and the workpiece by increasing the viscosity of the rubber above 4000 centipoises and to flexible elastic form so as to immobilize the particles; removing the magnetic rubber inspection record thus formed and inspecting for concentrations of the magnetizable particles to delineate flaws; and carrying out post-inspection procedures. Also disclosed are specific formulations and ingredients thereof, including delineation of components that cure the problems of the prior art.

17 Claims, No Drawings

CASTABLE MAGNETIC PARTICLE FLAW DETECTION COMPOSITION AND METHOD USING CONSTITUENTS THAT ARE NON-VOLATILE AND RESISTANT TO OXIDATION BELOW 100° F AND HAVING A VISCOSITY LESS THAN 12,000 CENTIPOISES

BACKGROUND OF THE INVENTION

1. Field of the Invention

This invention relates generally to a procedure for visually inspecting a given region of a workpiece having drilled holes or other metal surfaces. More particularly, this invention relates to inspection procedures and formulations wherein suitable organic mixtures, such as rubbers or polymerizing materials are admixed with sensitizing agents and magnetizable, or magnetic, particles are used in conjunction with applied magnetic fields of predetermined magnitude and duration to form cast replicas, or impressions, of the metallic surfaces, or regions, of a workpiece; the admixtures being curable, removable, and inspectable for anomalous alignment of the particles against a contrasting background to delineate flaws or potential flaws; such as cracks, scratches, tool marks, dimensional inaccuracies and subsurface flaws that may tend to develop in structurally deficient members.

2. Description of the Prior Art

The prior art has seen the development of many forms of nondestructive testing. One such method has been magnetic particle inspection. The most pertinent art of which we are aware is U.S. Pat. No. 3,862,047, entitled "Method and Composition for Detecting Flaws in Metallic Surfaces, Holes and Otherwise", inventors Henry J. Weltman, Mark T. Carrol, John E. Halkias, William T. Kaarlela, and Jack D. Reynolds, assigned to the General Dynamics Corporation, Fort Worth, Texas; and the descriptive matter of that patent is incorporated herein by reference for details omitted herefrom in the interests of brevity.

U.S. Pat. No. 3,862,047 contains an excellent discussion of the development and other pertinent references. As discussed therein, magnetic particle inspection of critical steel parts has been an accepted nondestructive testing practice within aerospace industries for many years. This is evidenced by the number of patents cited; namely, U.S. Pat. Nos. 2,601,212; 2,744,040; 2,791,561; 3,087,832; 3,345,564; and Noll Chemistry and Technology of Silicones, Academic Press, New York, New York, 1968, pages 397-9. Additional patents that are pertinent are British Pat. No. 933,701, U.S. Pat. Nos. 2,848,748; 3,445,759.

Of the methods disclosed, the most commonly known method previously used consisted of coating the area to be inspected with a suspension of magnetic iron oxide suspended in a volatile petroleum oxide type solvent or introducing the magnetic particles to the proposed area as a dry powder. After coating, and regardless of whether the magnetic particles were disseminated by the liquid or the powder, the area to be tested was magnetized in a known direction. The magnetic particles, upon application of the magnetic field, migrate to the secondary magnetic field created by any flaws or discrepancies that are present. The magnetic particles become aligned over any defect because of an interruption of the magnetic lines of flux in the component or area affected, thus disclosing the presence of the defect or irregularity. This process is generally not applicable to inspection of internal surfaces of holes and is necessarily limited to use of readily accessible surfaces.

Normal magnetic particle inspection provides visual indication of surface defects because the particles concentrate at the defective area. It is possible to enhance visibility by coating the magnetic particles with a dye, known in the industry as Magnaflux. Another process is known as Magnaglow in which the magnetic particles are coated with a flourescent dye and detection is accomplished under ultra-violet light. These methods did not provide a permanent record of the inspection. Other methods employed film forming constituents in which the magnetic particles were oriented in the magnetic field and a relatively rapidly drying film was used to preserve the record of the orientation of magnetic particles, although in a fragile type film. Moreover, these fragile films did not lend themselves to application in difficultly accessible areas, such as around holes or the like.

A further variation was employed in which a type of plastic, such as polyvinyl alcohol dispersed in a volatile solvent, was cast on top of the area to be inspected. When the solvent evaporated, the resultant layer was reinforced, removed, and the orientation of the magnetic particles detectable. These types of castings, while permanent, are, as compared to the method hereinafter disclosed, relatively difficult to remove. A further disadvantage is their limitation in use to top horizontal planes and lack of applicability in inspection of deep or threaded holes. Additionally, the volatile solvent is an undesirable feature.

The aforementioned U.S. Pat. No. 3,862,047 disclosed a method and composition for overcoming the disadvantages of the prior art. Specifically, the method and composition of that patent allowed inspecting any region of any part. Small flaws that require magnification for their detection could be delineated. The method allowed access to difficultly inspected positions such as interiorly of cavities, holes, and the like. Even that improved method had, however, some disadvantages. For example, the permanent record that was formed and removed from the region of the workpiece tended to have a portion of its diluent volatile so as to vaporize and cause shrinkage. Consequently, the mold was not as large as initially formed. Moreover, the constituents of the composition were oxidizable at temperatures below 100° F, and even at room temperatures, or less. Consequently, the materials became rancid, or were oxidized, and created an odor problem. In addition, constituents of the diluent tended to be exuded or secreted, as a liquid to form droplets on the exterior of the mold, or casting.

Thus, it can be seen that the prior art, even the improved method and composition in accordance with U.S. Pat. No. 3,862,047, did not provide a completely satisfactory long term solution.

SUMMARY OF THE INVENTION

Accordingly, it is a primary object of this invention to provide method and composition for forming a preservable record of the inspection for flaws in holes and other metal surfaces by forming cast replicas or impressions of the surface of the area of the workpiece to be inspected; yet, alleviating the difficulties and disadvantages of the prior art.

It is a specific object of this invention to provide a nondestructive inspection method accomplishing the first object, yet providing a permanent record that did not shrink, did not have objectionable odors because of rancidity, and did not "weep", or exude a liquid.

These and other objects will become apparent from the following descriptive matter.

In accordance with one embodiment of this invention, there is provided a method of preparing a preservable record of an inspection of a workpiece for flaws comprising a multi-step method as follows. First a polymeric rubber is prepared to have an initial viscosity of less than 1000 centipoises, remain below 4000 centipoises for a predetermined period of time and increase above 4000 centipoises after the predetermined period of time. The polymeric rubber consists essentially of only constituents that are not volatile below 100° F so as to resist shrinking of the final mold or casting; that are resistant to oxidation below 100° F so as to resist rancidity; and that are not exuded or excreted from the rubber as liquid. The polymerizing rubber has a first color for providing a contrasting background for magnetizable ferromagnetic particles. The polymerizing rubber having the desired characteristic is ordinarily prepared by mixing a highly viscous polymerizing rubber with a low viscosity diluent to obtain the desired results. Next, there is formed a magnetic rubber admixture by adding to the polymerizing rubber, particles capable of migrating in the rubber under the influence of a magnetic field of predetermined magnitude at viscosity below 4000 centipoises. The particles are sized within the range of about 0.5-50 microns; preferably about 1-10 microns, and have a second color that is different from the first color so as to afford a contrasting and visual indication of a concentration and alignment of the ferromagnetic particles in a final mold. The magnetic rubber admixture is applied to the workpiece in the region to be inspected so as to form a separable imprint thereof. If desired, suitable dams, or the like, may be employed to retain the magnetic rubber admixture in place initially. The magnetic field of the predetermined magnitude is applied to the region of the workpiece and to the magnetic rubber admixture before the polymerizing rubber has increased above 4000 centipoises in viscosity. The field is applied for sufficient time to effect migration and alignment of the ferromagnetic particles along any imperfection in the region of the workpiece. A magnetic rubber inspection record of the alignment of magnetic particles adjacent the interface between the magnetic rubber admixture and the region of the workpiece is formed by increasing the viscosity of the polymerizing rubber above 4000 centipoises and to elastic flexible form so as to immobilize ferromagnetic particles that may be aligned or concentrated along any such flaws. The magnetic rubber inspection record is removed and inspected for color contrast due to such concentration or of ferromagnetic particles. If desired, suitable optical magnification may be employed for the inspection. Finally, the post inspection procedures are carried out.

In another embodiment of this invention, there is provided a composition forming a room temperature vulcanizable casting material for precise visual inspection of magnetically inductive substances by application of the material directly to a workpiece to be inspected, solidifying in situ to elastic, flexible form and removing the casting for determining and permanently recording the presence of a flaw or flaws in the workpiece by migrations of magnetizable particles in the composition to the flawed area when the workpiece and casting material are subjected to magnetic flux. The composition comprises a base formulation having a proportion of about 100 parts by weight polymerizing rubber compound that is vulcanizable at room temperature by addition of suitable catalyst material thereto; a proportion of about 0.1 to about 10 parts by weight of ferromagnetic particles in the size range of about 0.8 to about 10 microns. When the ferromagnetic particles are sized to be about 1 part by weight of the rubber in the range of about 0.8 to about 1.2 microns ($\mu$) and two parts by weight of the rubber as larger sizes ranging from about 6 to about 8 microns, visual flaw identification and record sharpness are found to be enhanced. The particles are provided a second or contrasting color to that of the first color, i.e. of the rubber, to provide a visible difference or contrast between an accumulation of particles in an area of a detected flaw when the composition is cured or vulcanized. Advantageously, the smaller sized particles are mixed ferromagnetic oxides with the larger size particles being of metallic iron for optimum record quality.

The base formulation has a diluent that consists essentially of only constituents that are nonvolatile at temperatures below 100° F so as to resist shrinkage, that are not oxidizable at ordinary room temperature, so as to resist rancidity and that are not excreted from the permanent record upon storage. The diluent is a hydrophobic material that is compatible with the polymeric rubber, miscible with the rubber in all proportions from about 1 to 4 to about 4 to 1. The diluent has a sufficiently low viscosity that an admixture with a polymerizing rubber can be brought within a range of about 100-1000 centipoises before application to the workpiece. The composition includes, in addition to the base formulation, a proportion of about 0.2 to about 6 parts by weight per 100 parts of the base formulation of a catalyst comprising a material that will vulcanize the polymerizing rubber to flexible elastic form and viscosity above the viscosity at which the ferromagnetic particles do not migrate so as to preserve a record of the inspection.

Further objects accomplished by the inventive concepts herein are improved sensitivity (location of smaller flaws) and easier interpretation (improved contrast), together with a reduction in required magnetic flux density and rapid curing of the formulation to its elastic solid state.

DESCRIPTION OF PREFERRED EMBODIMENTS

Herein, the term "polymerizing rubber", or simply "rubber" is employed in its broad sense as comprising the polymerizing elastomers, whether or not diluent has been added. The polymerizing rubber, per se, and without diluent, should have the following desirable properties.

1. Its viscosity should not exceed 12,000 centipoises (120 poises) in order that appropriate diluting can achieve a viscosity in the range from about 100 to 1000 centipoises (1 to 10 poises) required for optimum formulation sensitivity.

2. Its color should be light to provide a contrast needed to observe the alignment of magnetic particles of a second color. Various colors, as well as transparent castings, were laboratory tested to determine the ease of recognition of flaws. When the formulation included white polymerizing rubber, the viewing and visual comfort to an inspector were optimum.

3. It should be compatible with an adjustable catalytic system to provide variable cure times in the range of about 10 minutes to about 5 hours. Faster cure times may reduce detection sensitivity or reliability and slower cure times can cause unnecessary delay; unless necessitated by temperature extremes.

4. It should cure at room temperature after catalyst is added. Use of elevated temperatures to vulcanize, or cure, can be used but is impractical in most large applications, as in the aerospace industries.

5. It should polymerize, or cure, independently of external moisture conditions. Single component rubbers were employed but required atmospheric conditions to be proper for curing satisfactorily. Internal areas of large casting may require several days to cure.

6. It should have a minimum adhesion to the surface of the workpiece and have maximum cohesion to enable easy removal of the cast replica providing the record of the inspection. Adhering elastomers may be used in conjunction with various release agents, but are generally less practical and satisfactory than the rubbers delineated hereinafter. It should vulcanize, or cure, to form a system that will retain its shape without having to be maintained in a heated condition during the time when the magnetizable particles will be migrating.

The various polymerizing rubbers, or elastomers, include poly (butadienecostyrene), butyl rubber, Neoprene, poly (butadienecoacrylonitrile), cis polybutadiene, poly (ethylene-co-propylene), poly (epichlorohydrin), polyurethane, polyacrylates, polysulfides, polyfluorinatedhydrocarbons, and silicone rubbers like polysiloxanes, polysilanes, and polysilazanes. Other castable material such as waxes and low melting plastics can be used, although they are disadvantageous. Of the foregoing materials, the polysiloxanes, or the so-called silicone rubbers, are superior and exhibit the desired properties. Particularly preferred is the dimethyl polysiloxanes having a viscosity in the range of 8000 to 12000 centipoises at 77° F. Of the commercially available silicone rubbers, the RTV silicone rubber V-54 from SWS Silicones Corporation, Adrian, Michigan, 49221, and the RTV 25 Silicone Rubber from General Electric have proven to be most desirable. Table 1 gives the properties of the RTV Silicone Rubber V-54.

TABLE I

| Typical Properties | |
|---|---|
| Uncatalyzed Base Compound | |
| Color | White |
| Viscosity, 77° F, cp | 8000–12000 |
| Specific Gravity | 1.18 |
| Density at 77° F, g/cu. in. | 19.3 |
| Working Time, hours, min.* | 1 |
| Tack Free Time, hours* | 3–4 |
| Shelf Life, months | 12 |
| Cured Rubber (Cured 7 days at 77° F and 50% R. H.) | |
| Hardness, Shore A | 47 |
| Tensile Strength, psi | 400 |
| Elongation, percent | 155 |
| Tear Resistance, Die B | 18 |
| Dielectric Strength | 530 volts/mil |
| Dielectric Constant, $10^1$ Hz | 3.13 |
| Dissipation Factor, $10^1$ Hz | .004 |
| Volume Resistivity | $1.23 \times 10^{15}$ Ohm-cm |

*Catalyzed with 0.3% CA Catalyst.
g = gram; cm = centimeter
cu = cubic; in. = inch
min. = minutes; R.H. = relative humidity
psi = pounds per square inch
Hz = Hertz; cp = centipoises The polymeric rubber must have a viscosity below about 4000 centipoises in order for the magnetizable ferromagnetic particles to migrate under the influence of a magnetic field. As a practical matter, the polymeric rubber should have a viscosity below 1000 centipoises initially and should not cure to above 4000 centipoises in less that about 4 minutes in order to allow time to be applied. In the preferred embodiments, it has been found that the initial viscosity will be in the range of 100–1000 centipoises and will take in excess of 10 minutes, still more preferably in excess of 15 minutes, to reach 4000 centipoises at room temperature. Cure time alone is not definitive, since a satisfactory final replica is requirement. Heretofore, pot life (as defined hereinafter) was only about 15 percent or less of cure time. It is necessary to have a pot life of at least 20–25 percent of cure time. This invention makes possible short time, or quick cast, embodiments having pot life up to about 40 percent of cure times. If the rubber has an initial viscosity of less than 100 centipoises, the replica castings made from the mixture will be flimsy and more easily torn than those in the preferred embodiment. It has been found possible to prepare castings with reinforcing materials such as plastic, paper, or fabric, but such systems have been found to be cumbersome and, in many cases, such as inspection of holes, impractical. If the admixture has a viscosity greater than about 1000 centipoises, the magnetic particle migration is considerably reduced resulting in less sensitivity in detecting flaws in the workpiece. Rubber having viscosity greater than 4000 centipoises when applied exhibits very little sensitivity. Expressed otherwise, if the viscosity is too high, migration of the magnetic, or ferromagnetic, particles is slowed down.

Magnetic particles comprise any of the magnetizable particles that will migrate in the rubber described under the influence of the magnetic field of a predetermined magnitude. As described in U.S. Pat. No. 3,862,047, black iron oxide, $Fe_3O_4$, is satisfactory. It is also possible to use metallic iron powder. The preferred magnetic particles comprise, however, a mixture of black oxides of iron, chromium, and cobalt and of metallic iron. The most satisfactory readily commercially available products are known as 10335 Black produced by Drakenfeld Division of Hercules, Inc., Wilmington, Delaware and the Carbonyl Iron E produced by General Aniline and Film Corporation, New York, New York.

As disclosed in U.S. Pat. No. 3,862,047, particles sized in the range 5–60 microns may be employed. It has been found preferable, however, to employ a powder, or particle size, in the range of about 0.5–50 microns. The best results are obtained with particle sizes in the range of about 0.8–10 microns. The 10335 Black has about 1 micron particle diameter (effective). The Carbonyl Iron E ranges from about 6 to about 8 microns in effective diameter. As is recognized, the term "effective diameter" comprises the diameter that would cause the particle to lodge on a particular size screen when subjected to a standard sieve analysis. The particularly preferred ferromagnetic particles are about one part of 10335 Black to about 2 parts Carbonyl Iron E and employed per 100 parts of the undiluted polymer rubber. This ratio was selected based on laboratory tests which showed that the 10335 Black produced very sharp discontinuity indications, but the background color was rather dark, causing a reduction in indication to background contrast. Carbonyl Iron E produced a very light background but the indications were less sharp. Therefore, mixtures of these 2 materials were tested in an effort to find the best ratio to produce maximum contrast. The best ratio was found to be the value stated. Particle sizes other than the range indicated produce results of reduced sensitivity. Some of the test results are summarized in Table II.

TABLE II

| Particle Composition | Effective Diameter (microns) | Sensitivity | Contrast |
|---|---|---|---|
| Iron Oxide | 0.5 | Fair | Sharp indication-dark background |
| Oxides of iron, chromium, cobalt | 1.0 | Excellent | Sharp indication-dark background |
| Oxides of iron, chromium, cobalt chromium | 1.5 | Good | Sharp indication-dark background |
| Iron Oxide | 10.0 | Fair | Medium indication-medium background |
| Iron Oxide | 50.0 | Poor | Fuzzy indication-medium background |
| Metallic Iron | 2-3 | Poor | Fuzzy indication-light background |
| Metallic Iron | 6-8 | Excellent | Fuzzy indication-light background |

The usable concentration range of magnetic particles is the range from about 0.1 to about 10 parts per weight of particles per 100 parts of the polymeric rubber base.

The preferred color of the mixed oxide particles is black. When the particles are mixed into the white polymer rubber, the resulting color is gray. The discontinuity indications in the cured replica castings are a sharp black against a gray background. Particles may be of other colors and the polymers may be of other colors than white; but, as indicated hereinbefore, tests show that the maximum contrast is obtained using black particles in white polymer rubber. Tests were made employing fluorescent particles that glow under ultraviolet light. The disadvantage of this system, however, was the heavy fluorescent background in the entire replica casting, resulting in a poor contrast.

Obtaining the proper viscosity and contrast requires employing a satisfactory diluent in most cases.

Any diluent that is miscible with the polymeric rubber and that can reduce the viscosity of the base polymer to the desired level would work. The diluent may comprise materials; such as, heavy hydrocarbon naphthas, alcohols, esters, ketones, and halogenated hydrocarbons that will mix with the polymeric rubber in all proportions in the ratio of 1 to 4 to 4 to 1. The diluents can reduce the viscosity to the desired level. As noted hereinbefore, when the diluents have room temperature volatile materials, the replica castings will shrink following cure and cause exudation of fluids in the form of liquids from the cured casting. Moreover, some diluents that are subject to oxidation produce rancidity and an unpleasant odor. Nonvolatile materials, such as ethylene glycol and glycerine, have also been evaluated but these materials were not miscible with the base made with the polymeric rubber in the desired proportion. Various silicone liquids such as the polysiloxanes can be employed if they can be obtained in a viscosity within the range of 5-20 centipoises. A particularly preferred diluent is dimethyl polysiloxane having a viscosity in the range of 5-20 centipoises. Specifically, a commercially available dimethyl polysiloxane is the Dow Corning 200 Fluid, available with either 10 centipoises or the 20 centipoises viscosities. The 5-20 centipoise range was selected after tests showed that diluents of less than 5 centipoises contained volatile components causing shrinkage of the castings; whereas diluents over 20 centipoises were less efficient in reducing the viscosity.

In the latter case, a larger ratio of diluent to the polymeric rubber was required and resulted in replica castings that were flimsy and easily torn.

Specifically, the diluent is employed in sufficient quantity to reduce the viscosity of the polymeric rubber to a range of about 100 to 1000 centipoises. The preferred polymeric rubber for forming the magnetic rubber admixture has an initial viscosity in the range of 500-600 centipoises. Exact ratio of diluent to the polymeric rubber is, of course, dependent upon the viscosities of the respective ingredients. For example, if the viscosity of the polymeric rubber is 10,000 centipoises and the viscosity of the diluent is 10 centipoises, then about 66 parts by weight of diluent added to 100 parts by weight of base rubber will produce a mixture having a viscosity of about 600 centipoises. The rapidity with which the rubber develops its viscosity depends upon the rate of curing, or vulcanizing, and that, in turn, depends, at least in part, upon the catalyst employed.

The catalyst employed will be the one that is compatible with the particular polymeric rubber. Typical catalysts include the thiozols, sulfenamides for catalyzing the polymerization or copolymerization of butadiene monomers; thiuramsulfide, dithicarbamates, and sulfur for catalyzing butyl rubber, zinc oxide, magnesium oxide, and ethylenethiourea for catalyzing Neoprene; toluenedisocyanate for catalyzing polyurethane; benzothiazyldisulfide, and tetraethylaminetriamine (TETA) for catalyzing the polyacrylates; manganese dioxide, magnesium dioxide, zinc peroxide, lead peroxide, morpholine, and p-quinonedioxime for catalyzing the polysulfides; and benzoyl peroxide, metallic soaps, dicumylperoxide, butylperbenzoate, and di-tertiary butyl peroxide for catalyzing the silicones, like polysilanes, polysiloxanes, and polysilazanes. In the field of the silicones, the preferred catalysts are metallic soaps, such as dibutyl tin dilaurate and stannous octoate. The amount of the catalyst will depend upon the rapidity with which the curing, or vulcanizing, is desired to take place. As indicated hereinbefore, ordinarily a proportion of from about 0.2 to about 6 parts by weight of catalyst are employed per 100 parts of the base formulation comprising the rubber, diluent and ferromagnetic particles.

The process of this invention involves the use of room temperature vulcanizing rubber of a light color, preferably white, containing black ferromagnetic powder to replicate the area to be inspected. A small magnetic field generated in the area to which the magnetic rubber has been applied causes the ferromagnetic particles to migrate; prior to setting up, or curing, of the mixture; to secondary magnetic fields created by cracks or other defects involving material integrity. Following cure, the solid rubber replica is removed from the surface being tested and a visual examination reveals not only a clearly discernable display of the cracks or flaws present, but a representation of other surface conditions such as smoothness, drill damage, alignment and dimensional accuracy. The method and formulation of this invention provide much superior replicas in that they do not shrink, do not develop rancidity, and do not exude liquids.

In the aforementioned U.S. Pat. No. 3,862,047, there were discussed important factors involved in the formulation of the polymerizing rubber that would allow magnetizable particles to migrate to cracks or other flaws causing variations in the magnetic flux gradient. Because of the importance, these factors will be briefly repeated herein for the reader's convenience.

1. Optimum concentration of magnetic particles: if too low, insufficient migration takes place; if too high, poor contrast results between the display of the flaw and the background color of the casting.

2. Optimum size of the magnetic particles: if too fine, the particles are less sensitive to magnetic attraction; if too coarse, sharp crack indications are not produced.

3. Optimum viscosity of the polymerizing rubber: if too high, magnetic particle migration will not take place; if too low, too strong a magnetic flux background obscures indications and causes reduced structural integrity of the replica casting. Readily available polymerizing rubber has viscosity that is too high so its viscosity is adjusted downwardly; ordinarily, by addition of diluents. As disclosed in U.S. Pat. No. 3,862,047, it was formerly thought that employing a diluent such as a silicone oil to dilute even the thinnest available silicone rubbers would require more silicone oil than was compatible with the rubber. Moreover, the results of casting would leave excessive residual silicone on the part, in accordance with the prior art tests and reasoning.

4. Optimum type and quantity of catalyst: if too fast curing, magnetic particle migration will be prematurely halted; if too slow, the inspection time will be unduly prolonged.

5. Cure stabilizer: In some instances, the cure rate of the formulation is highly dependent on relative humidity. In order to achieve consistency and dependable cure rates that are independent of relative humidity, a cure stabilizer has been developed. When the cure stabilizer is mixed into the formulation along with the catalyst, the effect of relative humidity is greatly reduced.

6. Blending of ingredients: magnetic particles must be dispersed in a manner to break up agglomerates without inducing a static charge or reducing particle size.

In U.S. Pat. No. 3,862,047, there were outlined in its Table I, three optional mixtures of base materials. This has been refined through experience and an optimum mixture such as shown in Table III, hereinafter, can be employed in most applications. In Table III, the proportions of the respective components are given in parts by weight (pts. by wt.); whereas the viscosity is given in centipoises (cp) and the dimensions of the particle diameters are given in microns ($\mu$).

TABLE III

| Components | Proportion(pts. by wt.) |
| --- | --- |
| Polymerizing rubber, max. viscosity ≃ 12000 cp. | 100 |
| Diluent, viscosity 5–20 cp. | sufficient to reduce viscosity of admixture with rubber to 500–600 cp. |

TABLE III-continued

| Components | Proportion(pts. by wt.) |
| --- | --- |
| Ferromagnetic particles | 1–5 |

In U.S. Pat. No. 3,862,047, there was included a Table II delineating the various processes for the various applications and mixtures. Further experience and refinements have indicated the following information is somewhat more useful in application of this invention.

The type and quantity of catalyst used to cure the formulation described in Table III herein depends upon the particular inspection task. Cure times from about 10 minutes to about 5 hours may be selected as described in Table IV hereafter. An important consideration for selecting the curing system is the duration of magnetization required for the particular application. Magnetic field strength and duration requirements are shown in Table V.

In Table IV, the formulation catalyst assumes the use of white dimethyl polysiloxane polymerizing rubber with a viscosity below 12,000 centipoises; since this is the optimum polymerizing rubber that has been found to date.

TABLE IV

| Cure System | Quantity of formulation (Table III) | Formulation Curing Systems | | Cure Stabilizer | Allowable Duration of Magnetism | Cure Time |
| --- | --- | --- | --- | --- | --- | --- |
| | | Catalyst | | | | |
| | | Type | Quantity | | | |
| Quick-cast | 10 ml. | dibutyl tin dilaurate stannous octoate | 15 drops 3 drops | none | 4 minutes | 10 min. |
| Standard | 10 ml. | dibutyl tin dilaurate | 15 drops | 2 drops. | 10–14 min. | 45–60 min. |
| Extended-2 hour | 10 ml. | dibutyl tin dilaurate | 5 drops | 2 drops | 20–30 min. | 1½ to 2½ Hr. |
| Extended-4 hour | 10 ml. | dibutyl tin dilaurate | 2 drops | 2 drops | 40–60 min. | 3 to 5 hr. |

TABLE V

MAGNETIC FIELD STRENGTH AND DURATION

| Inspection Area | Available Field Strength Gauss* | Corresponding Magnetizing Duration |
| --- | --- | --- |
| Holes (uncoated) | 75 | 30 seconds |
| Surfaces (uncoated) | 150 | 1 minute |
| | 100 | 2 minutes |
| | 50 | 10 minutes |
| | 20 | 30 minutes |
| Coated Areas | 50–600 | 1 to 60 minutes (dependent on thickness of coating) |

*Gauss measurement made with gaussmeter probe in air adjacent to test area.

Referring to Table IV; if, for example, an area to be inspected is very small and easily magnetized, the quick-cast curing system can be employed. The formulation then will cure and be ready for interpretation in about 10 minutes. In order to properly use the quick-cast, however, magnetization must be completed within 4 minutes from the time the catalyst is added. After that time, (called allowable duration of magnetization or pot life) the formulation becomes too thick to allow migration of the magnetic particles.

Normally, inspection is conducted using the standard cure system which allows about 10 to 14 minutes for completion of magnetization. The cure time for standard cure system is about 1 hour.

In some instances, the test area is difficult to magnetize and only a very weak magnetic field can be obtained. In this case, the period of magnetization must be extended to compensate for the weak magnetic field and one of the extended cure systems must be used.

The catalysts suggested in Table IV are not the only ones that are usable, as indicated from the general description hereinbefore. The dibutyl tin dilaurate and the stannous octoate are available from multiple commercial sources. For example, Thermolite 12 is a trade designation given to the preferred dibutyl tin dilaurate by its manufacturer, M & T Chemical Corporation, Rahway, New Jersey; while Nurocure 28 is a stannous octoate catalyst possessing the characteristics found to be the most desired for use with the silicone rubber. The Nurocure 28 is commercially available from Tenneco Chemicals, Inc., Long Beach, California.

Cure time, pot life, mix ratio and gauss application strengths and times specified herein have been arrived at by experimentation and experience and are considered as optimum rather than mandatory.

The composition hereinafter will be referred to generally as magnetic rubber for purposes of simplicity. This term is used in an effort to identify the composition without limiting it to any specific ratio of ingredients except as herein specified. While all formulations of the magnetic rubber contain essentially the same basic ingredients, different proportions, or ratios, are incorporated in accordance with applicable inspection requirements. As indicated hereinbefore, Table III gives the components and parts by weight of the optimum mixture of the magnetic rubber inspection material; Table IV shows available curing systems for the formulation; and Table V sets out optimum intensities and duration periods for application of magnetism.

It should be remembered that the magnetic rubber material may be admixed in a wider range of proportions than the limits set out hereinbefore. Testing over a long period of time has shown that there are ranges and variations allowable in the parts by weight ratio of the respective ingredients and in the ingredients themselves. Table VI hereinafter shows the range of the respective ingredients in the broad sense and also delineates specific examples on which exhaustive studies have been made. The specific concentrations and materials are those preferred and should serve as examples that can be used, within the generic listings.

As can be seen from the descriptive matter hereinbefore, the viscosity of the admixture of the ferromagnetic particles and the polymeric rubber, diluent and catalyst can be in the range between 100 to 12,000 centipoises, depending upon the stage of cure.

Numerous variables of formulations and application techniques are possible within the parameters specified. Formulation variables include types and concentrations of magnetic particles, diluents to control viscosity, types and quantities of catalysts and milling procedures to disperse the magnetic particles into the rubber. Application variables include the technique used in hole preparation (cleaning, taping, and placement of damming devices to hold the liquid rubber in horizontal voids), magnetization equipment and optimum fields, effect of coatings such as paints, flamesprayed metals, or platings, application time (pot life) and cure time for various catalyst systems, methods of examining replicas, methods of rating observed indications, post cleaning and demagnetization of inspected areas.

Uncoated metal requires a field of at least 20 gauss for satisfactory inspection. This field may be applied with permanent magnets or electromagnets. The proper field is conveniently introduced in D6 ac steel, for instance, by energizing a DC electromagnet at a high setting for a short time; for example, approximately 2 seconds; then turning it off. The resulting magnetic field remains at about 30 gauss. By adjusting the span of the magnet with auxiliary pole pieces, various configurations and varied areas can be covered, or an area covering several holes can be magnetized simultaneously.

Test specimens of magnetic metal coated with paint or plastic require more magnetism than bare surfaces. Such areas require 100 to 600 gauss, depending upon the thickness of the coating.

After removal of the cast replicas, they may be examined with a bench microscope. A power of 5 to 10X has proved best in applications to the present for viewing of the cast replica. In proper situations removal of the cast replica is abetted by use of a suitably sized pushing rod. In some circumstances (such as series of holes to be inspected), the test replicas may be connected by a continuous strip of the material, thus retaining several replicas in a fixed relationship.

Following inspections, by viewing of the cast replica, the area may be easily demagnetized (if required) by applying an AC electromagnet. A residual field of 0 to 1 gauss is easily attained. The test part may then be

TABLE VI

| Ingredients | | Composition | Parts by weight |
|---|---|---|---|
| Polymeric Rubber | General | Any castable material listed hereinbefore | 100 |
| | Specific | Dimethyl polysiloxane, room temperature curing silicone rubber, white, viscosity (max) to 12,000 centipoises | 100 |
| Diluent | General | Any material miscible with the base polymer which can reduce its viscosity to 100 to 4,000, preferably 1,000, centipoises | Sufficient to reduce viscosity of base polymer to 100 to 4,000 centipoises |
| | Specific | Dimethyl polysiloxane fluid, viscosity 5 to 20 centipoises | Sufficient to reduce viscosity of base polymer to 500 to 600 centipoises |
| Magnetic Particles | General | Any ferromagnetic material having particle diameter between 0.5 to 50 microns | 0.1 to 10 |
| | Specific | Combination of a mixture of black magnetic oxides of iron, chromium and cobalt (0.8 to 1.2 microns) and carbonyl iron (6 to 8 microns) | 1 mixed oxides 2 carbonyl iron |
| Catalyst | General | Any material which will cause formulation to cure within 10 min. to 5 hours. | Sufficient to cause formulation to cure within 10 minutes to 5 hours |
| | Specific | Dibutyl tin dilaurate Stannous octoate | 0.4 to 3.0 (20 to 150 drops) 0 to 0.4 (0 to 20 drops) | cleaned with a suitable solvent. Laboratory tests have shown that trichloroethylene effectively removes any residual silicones so that the part may be painted, plated, or coated with sealant and no loss of adhesion results.

Applications of the MRI (Magnetic Rubber Inspection) process herein are numerous. They include inspection of drilled holes for cracks before and after testing, evaluation of drilling and drill quality of holes, dimensions and fit-up checks in inaccessible areas and the monitoring of crack initiation and rate of crack propagation in fatigue testing. It is possible to inspect a wide range of hole sizes. The smaller rivet holes and threaded holes cannot be adequately inspected by any other means. Cast replicas have been used to demonstrate and provide a permanent record of undesirable misalignment in holes through multi-layer structural joints. An additional valuable use of the MRI process is in the monitoring of crack growth in drilled holes during fatigue testing. The cast replicas show the growth of cracks from initiation in tool marks to a predicted catastrophic failure location.

No minimum crack size limitations have been established. Even the very smallest of cracks, verified by sectioning and breaking open holes, have been detected. These have included cracks as small as 0.002 inches long and 0.0001 inches wide.

In practice, this invention is carried out similarly as described in U.S. Pat. No. 3,862,047. In that patent, the specific figures and methods of applying the magnetic rubber inspection system described herein were shown and described. That patent described application of the method to vertical and horizontal holes and the use of mylar or cellophane tape beneath a hole to allow emplacement of the admixture in accordance with the invention. Similarly, there is illustrated the use of mylar or cellophane tapes on a side, with or without an aluminum cup or similar damming device, to emplace the valcanizable admixture in horizontal holes or other difficultly accessible portions of a workpiece. Therein was described and this invention also employs use of a pin or needle to release air from cavities that might enclose trapped air as the admixture is poured into a mold region. If desired, vacuum putty or Dux-Seal may be used to make a dam or seal around a hole or the like, as described in that patent. During cure and while magnetism is applied to the structural elements particles in the cast magnetic rubber migrate and concentrate. Following cure they are easily removed to indicate the crack location, or other flaw.

Basically, the process of this invention is carried out by the following detailed steps.

First, the area to be inspected is cleansed of all dirt, sealants, or other contaminants. The cleansing may be accomplished by using a stiff brush and cheese cloth with trichloroethylene solvent. Lint may be removed with the assistance of compressed air. Any specific configuration to be inspected should be identified. The identification may become incorporated as part of the replica to be formed by the magnetic rubber.

The next step in the process is the addition of a catalyst to the rubber base along with stirring to assure a consistent and thorough mix. The magnetic rubber is poured into, over, and around the region of the workpiece to be inspected by using a cup to pour directly into the hole to be inspected or by using a plastic syringe for reaching difficultly accessible holes or areas. Air entrapment should be avoided by venting with pin holes. More holes should not be filled from a batch of magnetic rubber than can be magnetized within the formula pot life.

After pouring of the magnetic rubber, a magnetic field is applied to the area. This may be applied with permanent magnets or electromagnets as described hereinbefore.

The required magnetism to obtain an optimum magnetic field is described in Table V hereinbefore. For optimum results, the field strength depends upon the specimen material and the mixture used. The optimum results should be determined by examination of the magnetic field background in the replicas. If the background is too strong or weak, the applied field should be adjusted to obtain the optimum background for good reading of the replica. The "flash" method of magnetism has proven very successful on D6ac Steel and other similar metals possessing the characteristic of retaining residual magnetism. This method consists of applying a high magnetic field for a short time, as described hereinbefore. When using this method, it is necessary to wait at least 30 seconds before applying the magnetism to the area around the adjacent holes. For best results on the replica, the magnetic field should be applied to the area of the hole, delay 30 seconds, then apply a second field 90° from the original application.

Allowing sufficient time for curing is the next step and this will vary depending upon the chosen catalyst, formulation, and temperature.

As implied hereinbefore, the extended cure time resulting from low humidities can be overcome using cure stabilizers consisting essentially of water, alcohols, glycols, or the basic metal oxides such as zinc oxide and magnesium oxide and various combinations of these materials, and these materials diluted with hydrophyllic solvents. Miscible glycols are available but water alone requires a mutually miscible solvent for retention for long term use. The preferred cure stabilizer consists essentially of an admixture of about 15 percent (%) by volume of water in acetone. This is added to the formulation along with the catalyst to obtain the desired cure, as noted herein.

The preferred cure stabilizer is employed in a concentration within the range of about 0.1–1.0 percent by volume, with about 0.5 percent by volume preferred.

Upon curing, the resultant solid replicas are extracted. It may be necessary to use extraction rods to facilitate removal.

In certain instances where a plurality of holes are to be examined, a continuous strip of rubber may be cured so that the holes are removed in mass. This may be effected by pouring a strip of rubber between and over the holes at the time they are being filled.

Replicas may be removed by first removing the mylar tape, cups, dams, or the like, and then gently lifting the replicas from the open side while pushing from the closed side. Pushing rods of various sizes will facilitate this operation.

Following the removal of the cast replicas, they are examined. This is most effectively accomplished by the aid of a bench microscope with a magnification of about 5 to 10 times normal.

After the examination, the post-inspection procedure is performed. This consists of demagnetizing the area (if required) by applying an alternating current (AC) electromagnet. The residual field of 0 to 1 gauss is easily attained. The test part may then be rinsed with suitable solvent and cleansed. Laboratory tests have shown that trichloroethylene effectively removes the residual rubbers, particularly any residual silicone rubber and residual silicone oil so that the part may be painted, plated, or coated with sealant and no loss of adhesion results.

The following example, together with the respective examples given in the tables hereinbefore, will completely describe the invention and allow complete understanding thereof.

EXAMPLE 1

In this example, the silicone rubber V-54 from SWS Silicones Corporation was employed. It is a dimethyl polysiloxane silicone rubber that is white and has a viscosity in the range of 8,000–12,000 centipoises at 77° F. It was used in a portion of about 100 parts by weight. It was diluted with less polymerized dimethyl polysiloane having a viscosity of 5–20 centipoises. Sufficient diluent was employed to reduce the viscosity to about 500–600 centipoises and actually comprised about 66 parts by weight. To the admixture of the diluent and silicone rubber was added about one part by weight of mixed oxides of iron, cobalt, and chromium having particle diameters of about one micron (0.8 to 1.2 microns) and about 2 parts by weight of Carbonyl iron powder, having particle diameters of about 6–8 microns. To form the permanent inspection record, the resulting total admixture was catalyzed and poured into a hole in a structural steel part of an airplane. After the application of a magnetic field and cure and removal of the replica casting, even the very tiniest of cracks that were barely visible with 10 power magnification could be discerned. The larger cracks were readily discernable, both with 5 power magnification and even to the naked eye. Moreover, the same magnetic rubber inspection record delineated surface finish, dimensions and other microscopic imperfections. The magnetic inspection record was stored in sealed containers at ambient room conditions over a period of about six months and examined periodically during which time it remained stable without shrinking, without developing rancidity and without exuding the oils or other liquids that were found objectionable in the prior art.

EXAMPLE 2

In this example, the same composition employed in Example 1 was employed in conjunction with a cure stabilizer comprising 15% by volume of water in acetone. The cure stabilizer was employed in a proportion of 2 drops per 10 milliliters of the base composition. The resulting cure was relatively independent of a atmospheric moisture, or relative humidity, had the same dependable final results and could be stored for protracted intervals as desirably as in Example 1.

From the foregoing, it can be seen that this invention has been described with a certain degree of particularity. It is to be understood that the present disclosure is made only by way of example and that numerous changes in the details of employment and compositions can steps may be resorted to without departing from the spirit and scope of this invention.

What is claimed is:

1. A method of preparing a preservable and visible record of an inspection for determining the presence of a flaw in a workpiece comprising the steps of:

a. preparing a polymeric rubber that has an initial viscosity of less than about 1000 centipoises, remains below about 4000 centipoises for a predetermined time interval, and increases above about 4000 centipoises and to an elastic flexible form after said predetermined time interval; said rubber consisting essentially of only constituents that are nonvolatile below about 100° F so as to resist shrinking, that are resistant to oxidation below about 100° F so as to resist rancidity and that are not exuded in liquid form after curing to said elastic flexible form; said rubber having a first color for providing a constrasting background to make more readily visible a record of flaws;

b. forming a magnetic rubber admixture by adding to said rubber ferromagnetic particles capable of migrating in said rubber under the influence of a magnetic field of a predetermined magnitude at a viscosity below about 4000 centipoises; said particles being sized within the range of about 0.5 to about 50 microns and having a second color different from said first color so as to afford a visible indication of a concentration and alignment of said ferromagnetic particles;

c. applying said magnetic rubber admixture to said workpiece in the region to be inspected so as to form a separable imprint thereof;

d. applying a magnetic field of said predetermined magnitude to said region of said workpiece to be inspected and to said magnetic rubber admixture before said rubber has increased above said about 4000 centipoises viscosity and maintaining said magnetic field for a sufficient time interval to effect migration and alignment of said ferromagnetic particles along an imperfection at any flaw in said region of said workpiece;

e. forming a magnetic rubber inspection record of the alignment of said magnetic particles adjacent the interface between said magnetic rubber admixture and said region of said workpiece by increasing the viscosity of said rubber above about 4000 centipoises in situ to flexible elastic form so as to immobilize said ferromagnetic particles that have migrated to said flaw under the influence of said magnetic field;

f. removing said magnetic rubber inspection record from said workpiece; and g. inspecting said record for anomalous concentrations and alignments of ferromagnetic particles.

2. The method of claim 1 wherein said rubber has an initial viscosity in the range of about 100 to about 1000 centipoises.

3. The method of claim 2 wherein said polymeric rubber of step a is prepared by admixing a polymerizing rubber having a viscosity within the range of about 8,000 to about 12,000 centipoises with a diluent having a viscosity within the range of about 5–20 centipoises to obtain the desired initial viscosity and with a catalyst that will promote polymerization, that will allow time for the migration of the magnetic particles under the magnetic field, and that will effect increasing of the viscosity above about 4000 centipoises so as to immobilize said magnetic particles and form said record.

4. The method of claim 3 wherein said polymeric rubber comprises dimethyl polysiloxane silicone rubber, said diluent comprising dimethyl polysiloxane of lower polymerization and said catalyst is selected from the group consisting of dibutyl tin dilaurate and stannous octoate.

5. The method of claim 1 wherein said ferromagnetic particles have sizes within the range of about 0.8 to about 10.0 microns.

6. The method of claim 1 including the step of adding a cure stabilizer to said polymeric rubber so as to effect a more nearly uniform cure regardless of relative humidity.

7. The method of claim 6 wherein said cure stabilizer comprises about 15 percent by volume of water in acetone.

8. The method of claim 6 wherein said cure stabilizer is employed in a concentration within the range of about 0.1 to about 1.0 percent by volume of said rubber.

9. The method of claim 1 wherein said magnetic field of said predetermined magnitude is maintained at a level of at least about 20 gauss.

10. The method of claim 1 wherein said predetermined time interval is within the range of about 4 minutes to about 1 hour.

11. A composition forming a room temperature vulcanizable casting material for precise visual inspection of magnetically inductive substances by application of the material directly to a workpiece to be inspected, solidifying in situ to elastic flexible form and removing the casting, for determining and permanently recording the presence of flaw or flaws in the workpiece by migration of visible magnetizable particles in the composition to the flawed area when the workpiece and casting material are subjected to an effective magnetic flux comprising: a base formulation having:
   a. a proportion of about 100 parts by weight of polymeric rubber compound that is vulcanizable at room temperature by addition of a suitable catalyst material thereto; said rubber compound consisting essentially of only constituents that are non-volatile below about 100° F so as to resist shrinking, that are resistant to oxidation below about 100° F so as to resist rancidity, and that are not exuded from the rubber for a period of time; said rubber having a first color that is effective for providing for a contrast with ferromagnetic particles; said rubber compound having a viscosity less than about 12,000 centipoises;
   b. a proportion of about 0.1–10 parts by weight of visible ferromagnetic particles in the size range of about 0.8 to about 10 microns; said ferromagnetic particles having a second color that contrasts with said first color to facilitate visual observation of anomalous concentrations and alignments of said ferromagnetic particles;
   c. a diluent that contains only constituents that are non-volatile below about 100° F so as to resist shrinkage, that are resistant to oxidation below about 100° F so as to resist rancidity and that will not be exuded from the base formulation after it is removed from the surface of the workpiece; said diluent consisting essentially of a material that is compatible with said polymer rubber composition and miscible with said rubber in all proportions from about 1 to 4 to about 4 to 1; said diluent having a sufficiently low viscosity and being in a proportion such that its admixture with said rubber is brought to the range of from about 100 to about 1000 centipoises before application to the surface of said workpiece; and
   a proportion of about 0.2 to about 6 parts by weight per 100 parts of said base formulation of catalyst for vulcanizing said rubber compound to said flexible elastic form so as to immobilize said ferromagnetic particles that have migrated to any flaw under the influence of a magnetic field.

12. The composition of claim 11 wherein said polymeric rubber compound comprises a substantially linear dimethyl polysiloxane rubber having a viscosity below 12,000 centipoises and said diluent comprises dimethyl polysiloxane having a viscosity in the range of about 5 to about 20 centipoises and said proportion of said rubber and diluent are such that said base formulation has a visocisty within the range of about 100 to about 1000 centipoises initially; and said catalyst is selected from the group consisting of dibutyl tin dilaurate and stannous octoate and mixtures thereof and is present in proportion such that said base formulation has a cure time in the range of about 10 minutes to about 5 hours, at about 70° F to about 80° F and does not exceed about 4000 centipoises in less than about 20 percent of its cure time and cures to an elastic flexible form that is tack-free.

13. The composition of claim 12 wherein said base formulation does not exceed 4000 centipoises in less than 40 percent of its cure time.

14. The composition of claim 12 also including a cure stabilizer so as to effect a more nearly uniform cure rate regardless of ambient humidity.

15. The composition of claim 14 wherein said cure stabilizer consists essentially of about 15 percent by volume of water in acetone and is present in a concentration within the range of about 0.1 to about 1.0 percent by volume of said base formulation.

16. The composition of claim 11 wherein said ferromagnetic particles consist essentially of about ⅓ mixed ferromagnetic oxides and about ⅔ elemental metallic iron.

17. The composition of claim 16 wherein said mixed ferromagnetic oxides have particle sizes in the range of from about 0.8 to about 1.2 microns and said elemental metallic iron has particle sizes in the range of from about 6 to about 8 microns.

* * * * *